US00PP33691P2

(12) United States Plant Patent
Holtmaat

(10) Patent No.: US PP33,691 P2
(45) Date of Patent: Nov. 23, 2021

(54) ***ECHINACEA* PLANT NAMED 'FOUNT546'**

(50) Latin Name: ***Echinacea* hybrid**
Varietal Denomination: FOUNT546

(71) Applicant: Henricus Maria Joseph Holtmaat, Zuidwolde (NL)

(72) Inventor: Henricus Maria Joseph Holtmaat, Zuidwolde (NL)

(73) Assignee: AB-KWEKERSRECHTEN BV, Zuidwolde (NL)

( * ) Notice: Subject to any disclaimer, the term of this patent is extended or adjusted under 35 U.S.C. 154(b) by 0 days.

(21) Appl. No.: 17/185,918

(22) Filed: Feb. 25, 2021

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC ... A01H 5/02; A01H 5/00; A01H 6/14; A01H 6/1448
See application file for complete search history.

*Primary Examiner* — June Hwu
(74) *Attorney, Agent, or Firm* — Penny J. Aguirre

(57) ABSTRACT

A new cultivar of *Echinacea* plant named 'FOUNT546' that is characterized by its ray florets that are yellow-orange in color, its very floriferous flowering habit, and its compact, short plant habit.

2 Drawing Sheets

Botanical classification: *Echinacea* hybrid.
Variety denomination: 'FOUNT546'.

CROSS REFERENCE TO A RELATED APPLICATION

This application claims priority to European Community Plant Variety Office (CPVO) Plant Breeder's Rights Application No. 2020/2468. filed on Oct. 8, 2020, under 35 U.S.C. 119(f), the entire contents of which is incorporated by reference herein.

BACKGROUND OF THE INVENTION

The present invention relates to a new and distinct cultivar of *Echinacea* of hybrid origin and will be referred to hereafter by its cultivar name, 'FOUNT546'. 'FOUNT546' represents a new cultivar of coneflower, an herbaceous perennial grown for landscape use.

The new cultivar arose from an ongoing breeding program by the Inventor in Zuidwolde, The Netherlands with the objective of selecting new cultivars of *Echinacea* with strong plant habits and unique inflorescence colors. The new cultivar was selected as a unique seedling in a trial field by the Inventor in Zuidwolde, The Netherlands in July of 2018. The trial field had been planted with seed collected from numerous cultivars and proprietary *Echinacea* seedlings from the Inventor's breeding program. The parentage of 'FOUNT546' is therefore unknown.

Asexual propagation of the new cultivar was first accomplished by tissue culture using meristematic tissue in Heerhugowaard, The Netherlands in July of 2019 under the direction of the Inventor. Asexual propagation by tissue culture has determined that the characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'FOUNT546' as a unique cultivar of *Echinacea*.

1. 'FOUNT546' exhibits ray florets that are yellow-orange in color.
2. 'FOUNT546' exhibits a very floriferous flowering habit.
3. 'FOUNT546' exhibits a compact, short plant habit.

The new cultivar can be most closely compared to the cultivars 'Echgol243' (U.S. Plant Pat. No. 28,523) and 'Tweety' (U.S. Plant Pat. No. 28,952). 'Echgol243' and 'Tweety' are both similar to 'FOUNT546' in inflorescence shape. 'Echgol243' differs from 'FOUNT546' in having a taller and less compact plant habit, weaker stems that are floppy and ray florets that are orange with a tinged yellow base in color. 'Tweety' differs from 'FOUNT546' in having ray florets that have tips that are yellow-green in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosure includes but may not be limited to a website listings by Vitroflora.

BRIEF DESCRIPTION OF THE DRAWINGS

The plants in the accompanying photographs depict the characteristics of a two-year-old plant of 'FOUNT546' as grown in a 20-cm container in Zuidwolde, The Netherlands.

The photograph in FIG. 1 provides a side view of 'FOUNT546' in bloom.

Figure 1:
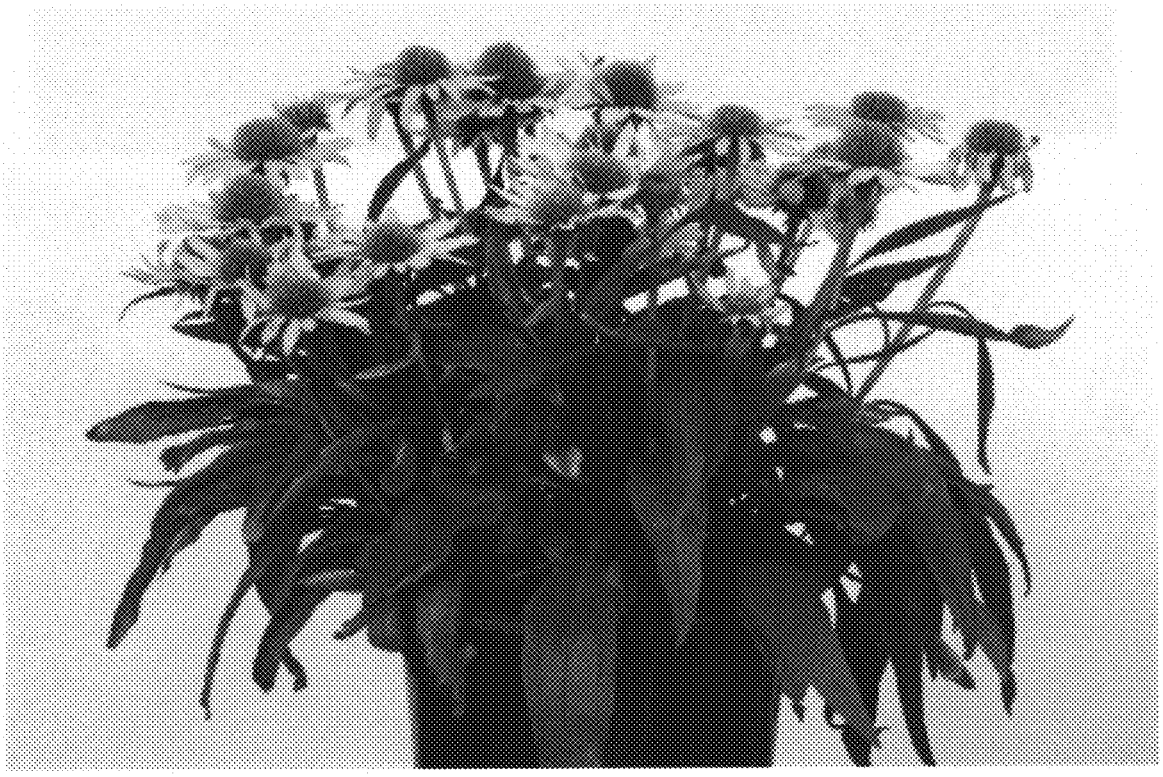
Figure 2:
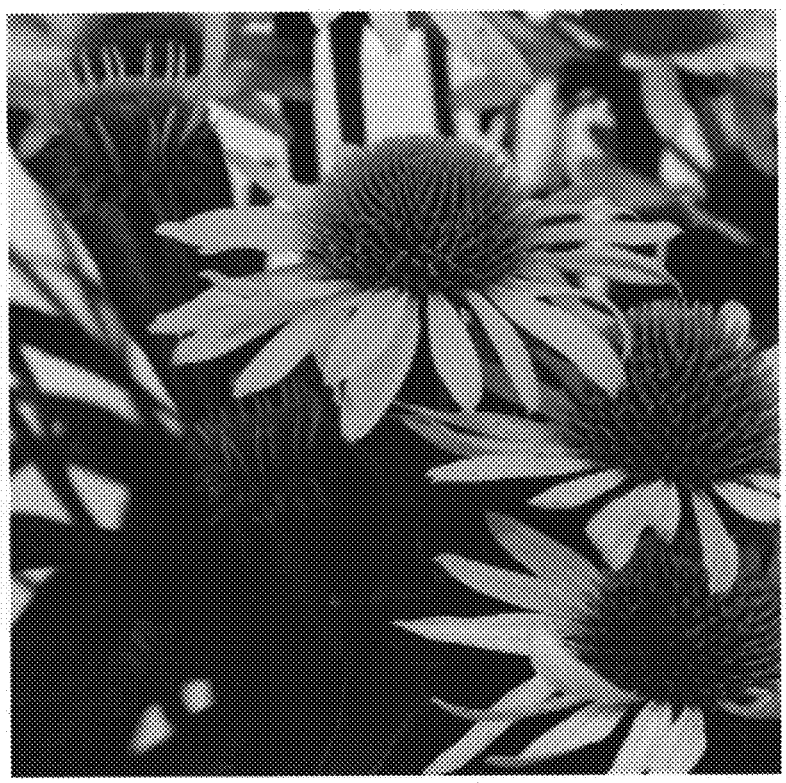

The photograph in FIG. 2 provides a close-up view of the inflorescences of 'FOUNT546'.

Figure 3:
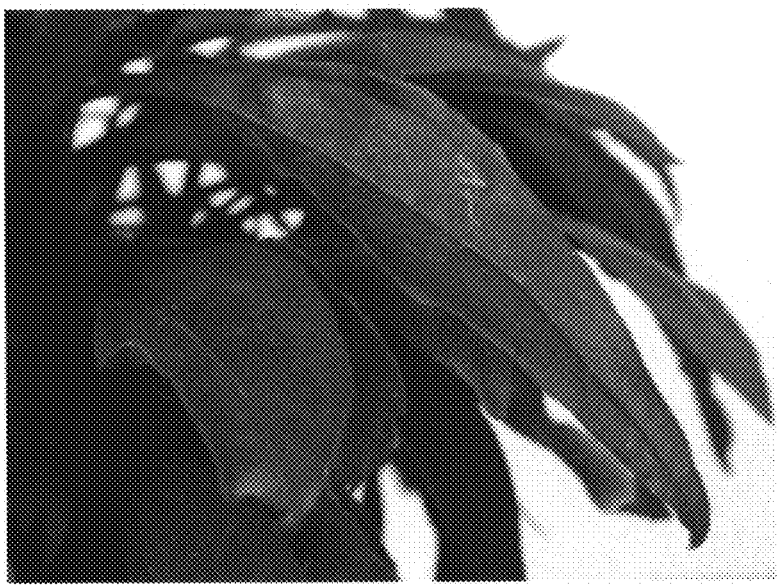

The photograph in FIG. 3 provides a close-up view of the foliage of 'FOUNT546'. The colors in the photograph may differ slightly from the color values cited in the detailed botanical description, which accurately describe the colors of the new *Echinacea*.

BOTANICAL DESCRIPTION OF THE PLANT

The plants in the accompanying photographs depict the characteristics of two-year-old plants of 'FOUNT546' as grown in 20-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of the Royal Horticultural Society, London, England, except where general color terms of ordinary dictionary significance are used.

General description:

*Blooming period*.—Approximately 10 weeks from summer and late summer (July until late September) in The Netherlands.

*Plant type*.—Herbaceous perennial.

*Plant shape*.—Flattened, broadly spreading.

*Plant habit*.—Compact and short.

*Height and spread*.—Average of 27.1 cm in height, 40.8 cm in width.

*Hardiness*.—At least in U.S.D.A. Zones 4 to 9.

*Diseases and pests*.—No resistance or susceptibility to pests or diseases has been observed.

*Root description*.—Fibrous.

*Propagation*.—Tissue culture.

*Root development*.—An average of 10 weeks for root development with a finished plant produced in about 3 months.

*Growth rate*.—Moderately vigorous.

Stem description:

*Shape*.—Rounded.

*Stem color*.—144A to 144C.

*Stem size*.—Average of 4 mm in diameter and an average of 19.5 cm in length.

*Stem surface*.—Rough to the touch, moderately covered with short strigose hairs; 0.2 mm in length, matches surface color.

*Stem strength*.—Strong.

*Stem aspect*.—Stems grow in an average angle of 10° from the base (0°=vertical).

*Branching*.—Main flowering stems grow from the base with a few lateral branches present, average of 15 primary branches, 1 branch per primary stem.

Foliage description:

*Leaf shape*.—Narrow ovate to narrow elliptic.

*Leaf division*.—Simple.

*Leaf base*.—Long attenuate.

*Leaf apex*.—Narrowly acute.

*Leaf venation*.—Pinnate, upper surface; 148B, lower surface; 146C.

*Leaf margins*.—Entire, slightly coarsely undulate.

*Leaf attachment*.—Petiolate.

*Leaf arrangement*.—Alternate.

*Internode length*.—An average of 2.2 cm.

*Leaf size*.—12.3 cm in length, 3.1 cm in width.

*Leaf color*.—Young upper surface; 137A, young lower surface; 138A, mature upper surface; NN137A, mature lower surface; 147B.

*Leaf surface*.—Both surfaces are slightly glossy, rough to the touch and moderately covered with very short strigose hairs; average length of 0.3 mm, too small to measure color.

*Petioles*.—On basal leaves an average of 16.1 cm in length and 1.5 mm in diameter, on cauline stem leaves V-shaped an average of 3.8 cm in length and 3.5 mm in diameter, surface is smooth and very sparsely covered with very short strigose hairs 0.3 mm in length and too small to measure color, color; upper surface 146C, margins 137B, lower surface 144B, margins 144A.

Inflorescence description:

*Type*.—Terminal capitulum, heterogamous with ray florets around the head margin and daisy-type disc florets in the center.

*Capitulum number*.—One terminal capitulum per lateral branch.

*Lastingness of inflorescence*.—About four weeks.

*Capitulum size*.—Matures to about 3.2 cm in height and 8.6 cm in diameter, disc is an average of 3.6 cm in diameter.

*Fragrance*.—Faint, sweet, pleasant.

*Involucral bracts or phyllary*.—Average of 64 arranged in 3 rows, up to 1 cm in length and 2.5 mm in width, cuneate base, acute apex, narrow ovate to lanceolate in shape, entire margins moderately, color; upper surface 137D, margined 137B, lower surface 137C, upper and lower surfaces smooth, very slightly glossy, sparsely covered with very short hairs, average length of hairs 0.3 mm, too small to measure color.

*Buds*.—Flattened globular in shape, up to 2.6 cm in diameter and 2 cm in length, color; 143A, immature ray florets 154C.

*Peduncle*.—Strong, straight on top of main (flowering) stem, average of 8.9 cm in length, 5 mm in diameter, color; 144C, blotches of 144A, surface is moderately covered with very short hairs an average length of 0.3 mm in length, too small to measure color.

*Ray florets*.—Rotate, average of 23 (varying between 16 and 30), whorled, oblanceolate in shape, average of 3.6 cm in length and 7 mm in width, un-deeply emarginate to un-deeply praemorse apex, cuneate base, entire margin, moderately drooping in an average angle of −5°, upper surface matte, velvety and glabrous, lower surface very slightly glossy, sparsely pubescent, color; upper surface when opening 15A, lower surface when opening 13B to 13C, upper surface when fully open 14A and 14B, lower surface when fully open 13C, upper surface fading to 4C, lower surface fading to 3D.

*Disc florets*.—Numerous, average of 120, tubular, lower 85% fused, base fused into tube, arranged spirally on disc, average of 1 cm in length and 2 mm in width, entire margin, both surfaces glabrous, moderately glossy, color; upper surface when opening and fully open 143A, mid-section 157A, base 145C, lower surface when opening and fully open upper half 143B, lower half transparent 145D, base 145A to 145B.

*Receptacle*.—Narrow ovate in shape, average of 1.5 cm in height and 8 mm in diameter, 155C in color.

*Receptacle spines*.—An average of 360 per disc floret, acicular in shape, acute apex, attenuate base, 1.2 cm in length, 2 mm in diameter, glabrous and glossy surface, color: apex; 15A, mid-section; 143B to 143C, base; 157A to 157B.

Reproductive organs (present on disc florets only):

*Gynoecium*.—Pistil; 1, 8 mm in length, stigma; unequal, decurrent, 4 mm in length, 153B, style; 6.5 mm in length and 153D in color, changing to 157A at the base, ovary; 157C to 157D in color.

*Androecium*.—Stamens; 5, filaments; 2 mm in length, 145D in color, anther; linear in shape, 3 mm in length and N200A in color, pollen; moderate, 21A in color.

*Fruit/seed*.—No fruit or seed detected to date.

It is claimed:

1. A new and distinct cultivar of *Echinacea* plant named 'FOUNT546' substantially as herein illustrated and described.

* * * * *